US009499821B2

(12) United States Patent
Kristie et al.

(10) Patent No.: US 9,499,821 B2
(45) Date of Patent: Nov. 22, 2016

(54) PREVENTING OR TREATING VIRAL INFECTION USING AN INHIBITOR OF THE LSD1 PROTEIN, A MAO INHIBITOR OR AN INHIBITOR OF LSD1 AND A MAO INHIBITOR

(71) Applicant: The United States of America, as represented by the Secretary, Department of Health and Human Services, Washington, DC (US)

(72) Inventors: Thomas Kristie, Silver Spring, MD (US); Yu Liang, Rockville, MD (US); Jodi Vogel, Bethesda, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 31 days.

(21) Appl. No.: 14/543,321

(22) Filed: Nov. 17, 2014

(65) Prior Publication Data
US 2015/0073039 A1 Mar. 12, 2015

Related U.S. Application Data

(63) Continuation of application No. 13/055,587, filed as application No. PCT/US2009/051557 on Jul. 23, 2009, now Pat. No. 8,916,596.

(60) Provisional application No. 61/111,019, filed on Nov. 4, 2008, provisional application No. 61/083,304, filed on Jul. 24, 2008.

(51) Int. Cl.
| | | |
|---|---|---|
| *A61K 48/00* | (2006.01) | |
| *C07H 21/02* | (2006.01) | |
| *C07H 21/04* | (2006.01) | |
| *A61K 31/42* | (2006.01) | |
| *C12N 15/113* | (2010.01) | |
| *A61K 31/00* | (2006.01) | |
| *A61K 31/137* | (2006.01) | |
| *A61K 31/15* | (2006.01) | |

(52) U.S. Cl.
CPC ........... *C12N 15/1137* (2013.01); *A61K 31/00* (2013.01); *A61K 31/137* (2013.01); *A61K 31/15* (2013.01); *A61K 31/42* (2013.01); *C12N 2310/14* (2013.01)

(58) Field of Classification Search
CPC ........... A61K 48/00; A61K 2039/505; C12N 15/113
See application file for complete search history.

(56) References Cited

U.S. PATENT DOCUMENTS

| 4,409,243 A | 10/1983 | Lieb |
| 2004/0198840 A1 | 10/2004 | Deloach |
| 2010/0015174 A1 | 1/2010 | Fernandez-Pol et al. |

FOREIGN PATENT DOCUMENTS

| EP | 649656 A1 | 10/1994 |
| JP | 2004292399 | 10/2004 |
| WO | WO 99/40908 A1 | 8/1999 |
| WO | WO 2006/071608 A2 | 7/2006 |
| WO | WO 2006/133396 A2 | 12/2006 |
| WO | WO 2007/006581 A2 | 1/2007 |
| WO | WO 2012/012627 A1 | 1/2012 |

OTHER PUBLICATIONS

AIDS treatment document from UCSF, downloaded from the internet on Jan. 18, 2012, pp. 1-2 updated Jan. 17, 2012, URL: http://www.ucsfhealth.org/conditions/aids/treatment.html.
Baas, "Transcription Prescription for herpes," *Scibx*, 2, 1-3 (2009), published online Dec. 3, 2009.
Chakraborty et al., "*N*-Acylanilines, Herbicide-CHA Chimera, and Amino Acid Analogues as Novel Chemical Hybridizing Agents for Wheat (*Triticum aestivum* L.)," *J. Agric. Food Chem.*, 53 (20), 7899-7907 (2005), published online Sep. 10, 2005.
Chang et al., "Histone Demethylase JMJD2A Regulates Kaposi's Sarcoma-Associated Herpesvirus Replication and Is Targeted by a Viral Transcriptional Factor," *J. Virol.*, 85 (7), 3283-3293 (2011), published online Jan. 12, 2011.
Chau et al., "Cell cycle association of the retinoblastoma protein Rb and the histone demethylase LSD1 with the Epstein-Barr virus latency promoter Cp," *J. Virol.*, 82 (7), 3428-3437 (2008), published online Jan. 23, 2008.
Cole, "Chemical probes for histone-modifying enzymes," *Nat. Chem. Biol.*, 4 (10), 590-597 (2008), published online Sep. 17, 2008.

(Continued)

*Primary Examiner* — Amy Bowman
(74) *Attorney, Agent, or Firm* — Leydig, Voit & Mayer, Ltd.

(57) ABSTRACT

An embodiment of the invention provides a method of preventing or treating a viral infection of a host, comprising administering to the host an effective amount of an inhibitor of the protein LSD1 and/or a monoamine oxidase inhibitor. Another embodiment of the invention provides a method of preventing or treating reactivation of a virus after latency in a host, comprising administering to the host an effective amount of an inhibitor of the protein LSD1 and/or a monoamine oxidase inhibitor. Another embodiment of the invention provides a method of preventing or treating a viral infection in a mammal that has undergone, is undergoing, or will undergo an organ or tissue transplant, comprising administering to the mammal an effective amount of an inhibitor of the protein LSD1 and/or a monoamine oxidase inhibitor before, during, and/or after the organ or tissue transplant. The viral infection may be due to a herpesvirus, such as herpes simplex virus type 1 (HSV-1) or type 2 (HSV-2), varicella zoster virus (VZV), or cytomegalovirus (CMV). The viral infection may also be due to an adenovirus, including types 1-5.

18 Claims, 7 Drawing Sheets

(56) References Cited

OTHER PUBLICATIONS

Cunliffe et al., "Novel Inhibitors of Prolyl 4-hydroxylase. 3. Inhibition by the Substrate Analogue N-Oxaloglycine and its derivatives," *J. Med. Chem.*, 35, 2652-2658 (1992).
Fauconnier, "Inhibitory action of succinic acid on the multiplication of influenza virus in embryonated eggs," *Comptes Rendus Hebdomadaires des Seances De L'Academie Des Sciences*, 239 (25), 1886-1888 (1954).
Gilmore et al., "Orthogonal Synthesis of Indolines and Isoquinolines via Aryne Annulation," *J. Am. Chem. Society*, 130 (5), 1558-1559 (2008), published online Jan. 15, 2008.
Gray et al., "Functional Characterization of JMJD2A, a Histone Deacetylase- and Retinoblastoma-binding Protein," *J. Biol. Chem.*, 280 (31), 28507-28518 (2005), published online May 31, 2005.
Hamada et al., "Design, Synthesis, Enzyme-Inhibitory Activity, and Effect on Human Cancer Cells of a Novel Series of Jumonji Domain-Containing Protein 2 Histone Demethylase Inhibitors," *J. Med. Chem.*, 53 (15), 5629-5638 (2010), published online Jul. 14, 2010.
Hamada et al., "Synthesis and activity of N-oxalylglycine and its derivatives as Jumonji C-domain-containing histone lysine demethylase inhibitors," *Bioorg. Med. Chem. Lett.*, 19 (10), 2852-2855 (2009), published online Mar. 26, 2009.
Hearn et al., "Cyclization of N-oxalyl-alpha-amino acid derivatives," Chemical Abstract No. 506665, published in 1968.
Hearn et al., "Cyclization of N-oxalyl-alpha-amino acid derivatives," *J. Org. Chem.*, 33 (10), 3980-3983 (1968).
Horig et al, "From bench to clinic and back: Perspective on the 1st IQPC Translational Research conference," *J. Transl. Med.*, 2 (1), 44, p. 1-8 (2004).
International Preliminary Report on Patentability, Application No. PCT/US2011/044835, dated Jan. 22, 2013.
International Search Report, Application No. PCT/US2009/051557, dated Feb. 26, 2010.
International Search Report, Application No. PCT/US2011/044835, dated Dec. 12, 2011.
Invitation to Pay Additional Fees and, Where Applicable, Protest Fee, Application No. PCT/US2011/044835, dated Oct. 12, 2011.
International Preliminary Report on Patentability, Application No. PCT/US2009/051557, dated Jan. 25, 2011.
King et al., "Quantitative high-throughput screening identifies 8-hydroxyquinolines as cell-active histone demethylase inhibitors," *PLoS One*, 5 (11) e15535, p. 1-12 (2010).
Kolb et al., "Association of the cellular coactivator HCF-1 with the Golgi apparatus in sensory neurons," *J. Virol.*, 82 (19), 9555-9563 (2008), published online Jul. 30, 2008.
Kristie et al., "Control of α-herpesvirus IE gene expression by HCF-1 coupled chromatin modification activities," *Biochim. Biohpys. Acta*, 1799 (3-4), 257-265 (2010), published online Aug. 12, 2009 (author manuscript).
Lee et al., "Histone H3 lysine 4 demethylation is a target of nonselective antidepressive medications," *Chem. Biol.*, 13 (6), 563-567 (2006) (with supplementary materials).
Liang et al., "Targeting the JMJD2 Histone Demethylases to Epigenetically Control Herpesvirus Infection and Reactivation from Latency," *Sci. Transl. Med.*, 5 (167ra5), 1-10 (2013) (with supplementary material).
Liang et al., "Inhibition of the histone demethylase LSD1 blocks alpha-herpesvirus lytic replication and reactivation from latency," *Nat. Med.*, 15 (11), 1312-1317 (2009) (with supplementary materials).
Liang et al., "Inhibition of the histone demethylase LSD1 represses α-herpesvirus lytic replication and reactivation from latency," Abstract International Herpesvirus Workshop (Jun. 2009).
Liang et al., "The histone demethylase LSD1 counters chromatin-mediated repression of infected α-herpesviruses," Abstract of Presentation at Itern Herpesvirus Meeting Jul. 26-Aug. 2, 2008.
Liang et al., "The JMJD2 family of histone demethylases cooperate with LSD1 to modulate repressive chromatin during HSV lytic infection and reactivation from latency," Abstract of Presentation at International Herpesvirus Workshop (published Jul. 20, 2010).
Lieb, "Invisible antivirals," *Int. J. Immunopharmac.*, 16 (1), 1-5 (1994).
Mecinović et al., "2-Oxoglutarate analogue inhibitors of prolyl hydroxylase domain 2," *Bioorganic & Med. Chem. Letters*, 19 (21), 6192-6195 (2009), published online Sep. 6, 2009.
Metzger et al., "LSD1 demethylates repressive histone marks to promote androgen-receptor-dependent transcription," *Nature*, 437 (7057), 436-439 (2005) (with supplementary materials).
Mimasu et al., "Structurally designed trans-2-phenylcyclopropylamine derivatives potently inhibit histone demethylase LSD1/KDM1," *Biochemistry*, 49 (30), 6494-6503 (2010).
Narayanan et al., "The coactivator host cell factor-1 mediates Set1 and MLL1 H3K4 trimethylation at herpesvirus immediate early promoters for initiation of infection," *PNAS*, 104 (26), 10835-10840 (2007) (and online supporting materials).
New York Times, "Herpes Simplex In-Depth Report," http://health.nytimes.com/health/guides/disease/herpes-simples/print.html, 1-8 (2012).
NIAID press release—Certain Antidepressants May Inhibit Herpesvirus Infection and Reactivation (Oct. 26, 2009).
Partial International Search, Application No. PCT/US2011/044835, dated Oct. 12, 2011.
Patel et al., "Infections in solid-organ transplant recipients," *Clin. Microbial. Rev.*, 10 (1), 86-124 (1997).
Presentation "The transcriptional coactivator HCF-1 mediates chromatin modifications for initiation of alpha herpesvirus infection," 13th International Conference on Immunobiology and Prophylaxis of Human Herpesvirus Infections (Nov. 5-8, 2007).
Presentation "The transcriptional coactivator HCF-1 mediates chromatin modifications for initiation of α-herpesvirus infection," Manipulation of Nuclear Processes by DNA Viruses conference (Mar. 3, 2008).
Rhode et al, "Hydroxyquinolines Inhibit Ribonucleic Acid-Dependent Deoxyribonucleic Acid Polymerase and Inactive Rous Sarcoma Virus and Herpes Simplex Virus," *Antimicrob. Agents Chemother.*, 10(2), 234-240 (Aug. 1976).
Rose et al., "Inhibitor Scaffolds for 2-Oxoglutarate-Dependent Histone Lysine Demethylases," *J. Med. Chem.*, 51 (22), 7053-7056 (2008), published online Oct. 23, 2008 (with supplementary material).
Rose et al., "Selective Inhibitors of the JMJD2 Histone Demethylases: Combined Nondenaturing Mass Spectrometric Screening and Crystallographic Approaches," *J. Med. Chem.*, 53 (4), 1810-1818 (2010), published online Jan. 20, 2010 (with supplementary material).
Schäfer et al., "Failure is an option: learning from unsuccessful proof-of-concept trials," *Drug Discov. Today*, 13 (21/22), 913-916 (2008).
Schmidt et al., "Trans-2-Phenylcyclopropylamine is a mechanism-based inactivator of the histone demethylase LSD1," *Biochemistry*, 46 (14), 4408-4416 (2007) (with supplementary materials), published online Mar. 17, 2007.
Shi et al., "Histone Demethylation Mediated by the Nuclear Amine Oxidase Homolog LSD1," *Cell*, 119 (7), 941-953 (2004).
Stitt, "Infection in the Transplant Recipient," Organ Transplant 2003 Medscape, http://www.medscape.com/viewarticle/45 1788_7 (2003).
Turk et al., "Antiretroviral activity and cytotoxicity of novel zidovudine (AZT) derivatives and the relation to their chemical structure," *Int. J. Antimicrob. Agents*, 20 (4), 282-288 (2002).
Vogel et al., "An HCF-1 protein complex couples Set1/MLL1 histone methyl-transferases with the histone demethylase LSD1," Abstract of Presentation at Itern Herpesvirus Meeting Jul. 26-Aug. 2, 2008.
Vogel et al., "HCF-1 mediated chromatin modulation during a-herpesvirus lytic infection and reactivation from latency," Abstract of Presentation at International Herpesvirus Workshop (published Jul. 22, 2011).

(56) References Cited

OTHER PUBLICATIONS

Whetstine et al., "Reversal of Histone Lysine Trimethylation by the JMJD2 Family of Histone Demethylases," *Cell*, 125 (3), 467-481 (2006), published online Apr. 6, 2006.

Whitlow et al., "Association of the transcriptional coactivator HCF-1 with immediate early gene promoters during initiation of HSV-1 reactivation from latency," Abstract International Herpesvirus Workshop Jun. 2009.

Whitlow et al., "Recruitment of the Transcriptional Coactivator HCF-1 to Viral Immediate-Early Promoters during Initiation of Reactivation from Latency of Herpes Simplex Virus Type 1," *J. Virol.*, 83 (18), 9591-9595 (2009) (with supplementary materials), published ahead of print Jul. 1, 2009.

Wissman et al., "Cooperative demethylation by JMJD2C and LSD1 promotes androgen receptor-dependent gene expression," *Nat. Cell Biol.*, 9 (3), 347-353 (2007), published online Feb. 4, 2007.

Written Opinion of the International Searching Authority No. PCT/US2009/051557, Jan. 24, 2011.

Written Opinion of the International Searching Authority No. PCT/US2011/044835, dated Jan. 22, 2013.

US 9,499,821 B2

PREVENTING OR TREATING VIRAL INFECTION USING AN INHIBITOR OF THE LSD1 PROTEIN, A MAO INHIBITOR OR AN INHIBITOR OF LSD1 AND A MAO INHIBITOR

CROSS-REFERENCE TO RELATED APPLICATIONS

This patent application is a continuation of U.S. patent application Ser. No. 13/055,587, which is a U.S. National Phase of International Patent Application No. PCT/US2009/051557, filed Jul. 23, 2009, which claims the benefit of U.S. Provisional Patent Application No. 61/083,304, filed Jul. 24, 2008 and 61/111,019, filed Nov. 4, 2008, all of which are incorporated by reference.

SEQUENCE LISTING

Incorporated by reference in its entirety herein is a computer-readable nucleotide/amino acid sequence listing identified as follows: One 10,310 Byte ASCII (Text) file named "718927SequenceListing_ST25.txt," created May 12, 2016.

BACKGROUND OF THE INVENTION

Methylation of chromatin, a reversible modification mediated by histone methyl-transferases and demethylases, is a significant component of cellular transcriptional regulation. Such chromatin modifications also impact invading viral pathogens that rely upon the host cell transcriptional apparatus. During infection of viruses, the assembly and modification of chromatin on the viral genomes has the potential to determine the progression of lytic infection as well as control recurrent latency-reactivation cycles.

A need continues to exist for methods of preventing or treating a viral infection of a host.

BRIEF SUMMARY OF THE INVENTION

An embodiment of the invention provides a method of preventing or treating a viral infection of a host, comprising administering to the host an effective amount of an inhibitor of the protein LSD1 and/or a monoamine oxidase inhibitor.

Another embodiment of the invention provides a method of preventing or treating reactivation of a virus after latency in a host, comprising administering to the host an effective amount of an inhibitor of the protein LSD1 and/or a monoamine oxidase inhibitor.

Another embodiment of the invention provides a method of preventing or treating a viral infection in a mammal that has undergone, is undergoing, or will undergo an organ or tissue transplant, comprising administering to the mammal an effective amount of an inhibitor of the protein LSD1 and/or a monoamine oxidase inhibitor before, during, and/or after the organ or tissue transplant.

DETAILED DESCRIPTION OF THE INVENTION

Figure 1:
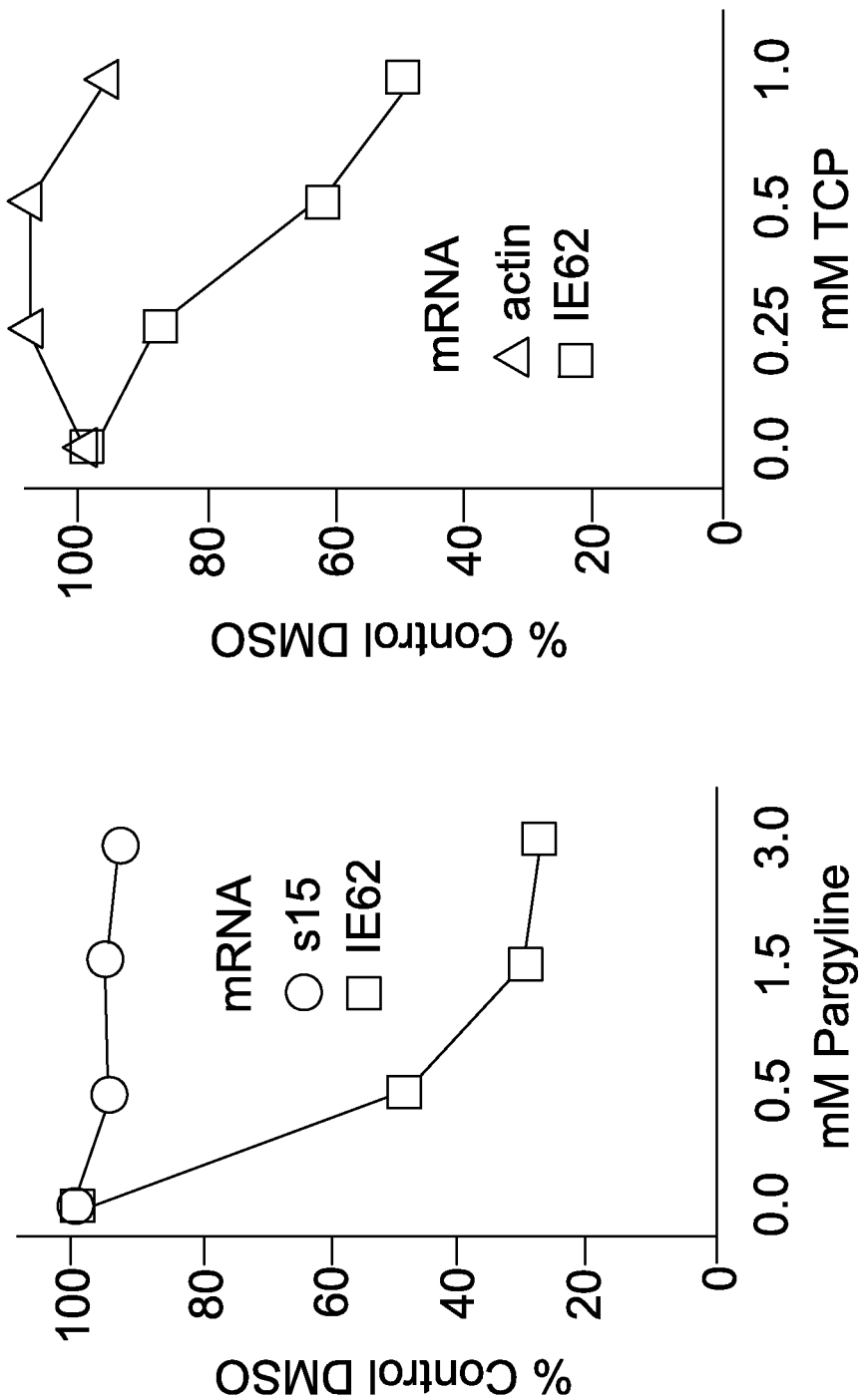
FIG. 1 shows treatment of varicella zoster virus (VZV)-infected cells with monoamine oxidase inhibitors resulted in a dose dependent decrease in viral mRNA and IE proteins. The data were generated using qRT-PCR analysis of the IE62 and control (s15, actin) mRNA levels in cells infected with VZV for 4 hrs in the presence of increasing amounts of Pargyline (Left panel) or Tranylcypromine (TCP, Right panel). The results are represented as the percent of levels in dimethyl sulfoxide (DMSO) treated cells.

An embodiment of the invention provides a method of preventing or treating a viral infection of a host, comprising administering to the host an effective amount of an inhibitor of the protein LSD1 and/or a monoamine oxidase inhibitor.

Another embodiment of the invention provides a method of preventing or treating reactivation of a virus after latency in a host, comprising administering to the host an effective amount of an inhibitor of the protein LSD1 and/or a monoamine oxidase inhibitor.

Another embodiment of the invention provides a method of preventing or treating a viral infection of a host, comprising administering to the host an effective amount of an inhibitor of the protein LSD1 and/or a monoamine oxidase inhibitor, wherein the administration of the inhibitor(s) prevents or treats the viral infection.

Another embodiment of the invention provides a method of preventing or treating reactivation of a virus after latency in a host, comprising administering to the host an effective amount of an inhibitor of the protein LSD1 and/or a monoamine oxidase inhibitor, wherein the administration of the inhibitor(s) prevents or treats the viral reactivation.

A "host" may be considered a single cell, a tissue, an organ, or an individual organism, such as a mammal. The mammal can be any suitable mammal, such as a mammal selected from the group consisting of a mouse, rat, guinea pig, hamster, cat, dog, pig, cow, horse, and primate. In one embodiment, the mammal is a human.

A viral infection is present in a host when a virus replicates itself within the host. A virus contains its own genetic material but uses the machinery of the host to reproduce. The virus may reproduce immediately, whereby the resulting virions destroy a host cell to attack additional cells. This process is the viral lytic cycle. Alternatively, a virus may establish a quiescent infection in a host cell, lying dormant until environmental stimuli trigger re-entry into the lytic replication cycle. Such re-emergence or re-entry into the lytic replication cycle is termed reactivation.

The viral infection may be due to a herpes viral infection. The herpesvirus may be, e.g., herpes simplex virus (HSV) type 1, herpes simplex virus type 2, varicella zoster virus (VZV), such as VZV-1, or cytomegalovirus. The viral infection may be due to an adenovirus infection. The adenovirus may be any adenovirus, including, e.g., Types 1-5. One embodiment is where the adenovirus is Type 5.

Herpes simplex virus type 1 (HSV-1) and type 2 (HSV-2) are common infections worldwide. HSV-2 is the cause of most genital herpes and is generally sexually transmitted. In contrast, HSV-1 is usually transmitted via nonsexual contacts. Preexisting HSV-1 antibodies can alleviate clinical manifestations of subsequently acquired HSV-2. Furthermore, HSV-1 has become an important cause of genital herpes in some developed countries. Varicella Zoster virus characteristically produces vesicular pruritic disseminated lesions at varying degrees of maturity. It occurs most frequently in children, with prodromal malaise, pharyngitis and rhinitis, usually with fever and pruritus (chickenpox). Varicella Zoster virus may cause more severe illness in adults, where the lesions are localized and painful, and often involve the trunk (shingles).

Another embodiment of the invention provides a method of preventing or treating a viral infection in a mammal that has undergone, is undergoing, or will undergo an organ or tissue transplant, comprising administering to the mammal an effective amount of an inhibitor of the protein LSD1 and/or a monoamine oxidase inhibitor before, during, and/or after the organ or tissue transplant. A non-limiting example would be to administer an effective amount of an inhibitor of the protein LSD1 and/or a monoamine oxidase inhibitor to a mammal receiving (or that has received) an organ or tissue known or suspected to be infected with virus. Therefore, should the organ or tissue comprise virus in the latent state, the mammal may still have the transplant, allowing the mammal to receive a potentially life-saving transplant while not having to destroy the organ or tissue.

Another embodiment of the invention provides a method of preventing or treating a viral infection in a mammal that has undergone or will undergo an organ or tissue transplant, comprising administering to the mammal an effective amount of an inhibitor of the protein LSD1 and/or a monoamine oxidase inhibitor before, during, and/or after the organ or tissue transplant, wherein the administration of the inhibitor(s) prevents or treats the viral infection.

Any suitable monoamine oxidase inhibitor (MAOI) can be used in the inventive methods. Examples of MAOIs include pargyline, phenelzine, tranylcypromine, isocarboxazid, moclobemide, selegiline, nialamide, and toloxatone. In some embodiments of the invention, the MAOI can be tranylcypromine, pargyline, phenelzine, isocarboxazid, or selegiline.

Other inhibitors of LSD1 can be used. A suitable inhibitor includes a nucleic acid (e.g., RNA), protein, small molecule, or antibody that specifically binds to LSD1, inhibits translation of LSD1, inhibits transcription of LSD1, or otherwise interferes with the biological expression and/or activity of LSD1. One such inhibitor is an RNA interference (RNAi) inhibitor. The RNAi inhibitor may comprise any RNA sequence that is complementary to the target LSD1 nucleic acid or a portion thereof. Antibodies and RNAi inhibitors of LSD1 can be prepared using routine techniques. Furthermore, suitable inhibitors can be determined using routine techniques, such as employing the EpiQuik Histone Demethylase LSD1 Inhibitor Screening Assay Kit (Epigentek Group, Brooklyn, N.Y.) or the LSD1 Inhibitor Screening Assay Kit (Cayman Chemical Company, Ann Arbor, Mich.).

Without intending to be bound by any theory, HCF-1 is a cellular transcriptional coactivator that is required for the expression of the immediate early genes (IE), such as the IE genes of α-herpesviruses HSV-1 and VZV-1 during the initiation of lytic infection. Viruses, such as HSV and VZV, utilize virion-encapsidated transcriptional activators to recruit the HCF-1-Set/MLL1 histone methyl-transferase (HMT) complexes to the viral IE promoters, resulting in histone H3-lysine 4 (H3K4) trimethylation and initiation of IE gene transcription. Furthermore, depletion of HCF-1 results in an increase in the levels of repressive histone H3-lysine 9 (H3K9) methylation, providing a central role for HCF-1 in modulating chromatin modifications that determine viral gene expression. A description of the role of HCF-1 in reactivation from latency is set forth in Whitlow et al. (J. Virol., 2009; Epub 0:JV1.01115-09v1).

LSD1 (also known as BHC110) interacts with HCF-1 and has been shown to possess H3K9 demethylase activity which is important for the activation of nuclear hormone receptor-dependent transcription, cell fate determination, and cell cycle progression. LSD1 demethylates lysine residues via a flavin-adenine-dinucleotide-dependent reaction that is inhibited by MAOIs.

An inhibitor of LSD1 and/or a MAOI can be administered in a composition (e.g., pharmaceutical composition) that can comprise at least one carrier (e.g., a pharmaceutically acceptable carrier), as well as other therapeutic agents (e.g., other inhibitors of LSD1 and/or other MAOIs). The composition can be administered by any suitable route, including parenteral, topical, oral, or local administration. One embodiment of the invention is topical administration of an inhibitor of LSD1 and/or a MAOI. Such topical administration may be accomplished using a cream or lotion formulation for, e.g., the clearance of cold sores (HSV-1), genital sores (HSV-2), or shingles (VZV).

The pharmaceutically acceptable carrier (or excipient) is preferably one that is chemically inert to the MAOI and/or inhibitor of LSD1 and one that has little or no side effects or toxicity under the conditions of use. Such pharmaceutically acceptable carriers include, but are not limited to, water, saline, Cremophor EL (Sigma Chemical Co., St. Louis, Mo.), propylene glycol, polyethylene glycol, alcohol, and combinations thereof. The choice of carrier will be determined in part by the particular MAOI and/or inhibitor of LSD1 as well as by the particular method used to administer the composition. Accordingly, there is a wide variety of suitable formulations of the composition.

Preservatives may be used in the pharmaceutical composition. Suitable preservatives may include, for example, methylparaben, propylparaben, sodium benzoate, and benzalkonium chloride. A mixture of two or more preservatives optionally may be used. The preservative or mixtures thereof are typically present in an amount of about 0.0001% to about 2% by weight of the total composition.

Suitable buffering agents may be used in the pharmaceutical composition and may include, for example, citric acid, sodium citrate, phosphoric acid, potassium phosphate, and various other acids and salts. A mixture of two or more buffering agents optionally may be used. The buffering agent or mixtures thereof are typically present in an amount of about 0.001% to about 4% by weight of the total composition.

The following formulations for oral, aerosol, parenteral (e.g., subcutaneous, intravenous, intraarterial, intramuscular, intradermal, interperitoneal, and intrathecal), and rectal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art. A component of the formulation may serve more than one function.

The inhibitors of LSD1 and/or MAOIs, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inhibitors of LSD1 and/or MAOIs may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethylenegly-col) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations may include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets.

The inhibitors of LSD1 and/or MAOIs may be administered as an injectable formulation. The requirements for effective pharmaceutical carriers for injectable compositions are well known to those of ordinary skill in the art. See Pharmaceutics and Pharmacy Practice, J. B. Lippincott Co., Philadelphia, Pa., Banker and Chalmers, eds., pages 238-250 (1982), and ASHP Handbook on Injectable Drugs, Toissel, 4th ed., pages 622-630 (1986).

Topical formulations, including those that are useful for transdermal drug release, are well known to those of skill in the art and are suitable in the context of embodiments of the invention for application to skin.

The concentration of a compound of embodiments of the invention in the pharmaceutical formulations can vary, e.g., from less than about 1%, usually at or at least about 10%, to as much as 20% to 50% or more by weight, and can be selected primarily by fluid volumes, and viscosities, in accordance with the particular mode of administration selected.

Methods for preparing administrable (e.g., parenterally administrable) compositions are known or apparent to those skilled in the art and are described in more detail in, for example, Remington: The Science and Practice of Pharmacy, Lippincott Williams & Wilkins, 21st ed. (2005).

In addition to the aforedescribed pharmaceutical compositions, the inhibitors of LSD1 and/or MAOIs thereof can be formulated as inclusion complexes, such as cyclodextrin inclusion complexes, or liposomes. Liposomes can serve to target the MAOI and/or inhibitor of LSD1 to a particular tissue. Liposomes also can be used to increase the half-life of the MAOI and/or inhibitor of LSD1. Many methods are available for preparing liposomes, as described in, for example, Szoka et al., Ann. Rev. Biophys. Bioeng., 9, 467 (1980) and U.S. Pat. Nos. 4,235,871, 4,501,728, 4,837,028, and 5,019,369.

When inhibitors of LSD1 and/or MAOIs are administered with one or more additional therapeutic agents, including additional inhibitors of LSD1 and/or MAOIs as the additional therapeutic agents, one or more additional therapeutic agents can be coadministered to the mammal. By "coadministering" is meant administering one or more additional therapeutic agents and the inhibitors of LSD1 and/or MAOIs sufficiently close in time such that the inhibitors of LSD1 and/or MAOIs can enhance the effect of one or more additional therapeutic agents. In this regard, the inhibitors of LSD1 and/or MAOIs can be administered first and the one or more additional therapeutic agents can be administered second, or vice versa. Alternatively, the inhibitors of LSD1 and/or MAOIs and the one or more additional therapeutic agents can be administered simultaneously.

The delivery systems useful in the context of embodiments of the invention may include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain composition embodiments of the invention.

Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480.

In addition, pump-based hardware delivery systems can be used, some of which are adapted for implantation.

The terms "treat," "prevent," and "inhibit" as well as words stemming therefrom, as used herein, do not necessarily imply 100% or complete treatment, prevention, or inhibition. Rather, there are varying degrees of treatment, prevention, or inhibition of which one of ordinary skill in the art recognizes as having a potential benefit or therapeutic effect. In this respect, the inventive methods can provide any amount of any level of treatment, prevention, or inhibition of a condition associated with, e.g., LSD1 activity, such as demethylation of histones, in a host or mammal. Furthermore, the treatment, prevention, or inhibition provided by the inventive methods can include treatment, prevention, or inhibition of one or more conditions or symptoms of the disease being treated, prevented, or inhibited. Also, for purposes herein, "prevention" or "inhibiting" can encompass delaying the onset of the disease or a symptom or condition thereof.

An "effective amount" refers to a dose that is adequate to prevent, treat, or inhibit a condition associated with, e.g., LSD1 activity. Amounts effective for a therapeutic or prophylactic use will depend on, for example, the stage and severity of the disease or disorder being treated, the age, weight, and general state of health of the patient, and the judgment of the prescribing physician. The size of the dose will also be determined by the compound selected, method of administration, timing and frequency of administration as well as the existence, nature, and extent of any adverse side-effects that might accompany the administration of a particular compound and the desired physiological effect. For example, the dose of the inhibitor to be administered can be about 0.1 mg to 10 g per day (e.g., 0.5 mg, 1 mg, 5 mg, 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 2 g, 3 g, 4 g, 5 g, 6 g, 7 g, 8 g, 9 g, or ranges of any of the values described herein). Alternatively, the dose of inhibitor to be administered can be 0.001 mg/kg to 200 mg/kg per day (e.g., 0.01 mg/kg, 0.05 mg/kg, 0.1 mg/kg, 0.5 mg/kg, 1 mg/kg, 5 mg/kg, 10 mg/kg, 50 mg/kg, 100 mg/kg, 150 mg/kg, or ranges of any of the values described herein). It will be appreciated by one of skill in the art that various diseases or disorders could require prolonged treatment involving multiple administrations, perhaps using inhibitors of LSD1 and/or monoamine oxidase inhibitors in each or various rounds of administration.

A number of transfection techniques are generally known in the art (see, e.g., Graham et al., Virology, 52: 456-467 (1973); Sambrook et al., Molecular Cloning: A Laboratory Manual, 3rd ed., Cold Spring Harbor Press, Cold Spring Harbor, N.Y. 2001; Davis et al., Basic Methods in Molecular Biology, Elsevier (1986); and Chu et al., Gene, 13: 97 (1981). Transfection methods include calcium phosphate co precipitation (see, e.g., Graham et al., supra), direct micro injection into cultured cells (see, e.g., Capecchi, Cell, 22: 479-488 (1980)), electroporation (see, e.g., Shigekawa et al., BioTechniques, 6: 742-751 (1988)), liposome mediated gene transfer (see, e.g., Mannino et al., BioTechniques, 6: 682-690 (1988)), lipid mediated transduction (see, e.g., Felgner et al., Proc. Natl. Acad. Sci. USA, 84: 7413-7417 (1987)), and nucleic acid delivery using high velocity microprojectiles (see, e.g., Klein et al., Nature, 327: 70-73 (1987)).

The following examples further illustrate the invention but, of course, should not be construed as in any way limiting its scope.

EXAMPLES

Cell culture and viral infections: HeLa, BS-C-1, CV-1, Vero, MeWo, VZV (Ellen), and adenovirus type 5 stocks were obtained from American Type Culture Collection (ATCC). HSV-1 strain 17 was provided by N. Fraser (University of Pennsylvania School of Medicine). HSV (strain 17) infections were done by exposing uninfected cells to HSV infected cell lysates in DMEM medium containing 1% fetal bovine serum. At 1 hr post infection, the medium was replaced with DMEM containing 10% serum and incubation was continued. VZV infections were done by directly overlaying VZV infected BS-C-1 cells onto naïve cells. MCF7 inducible LSD1 shRNA cells were provided by X. Chen (University of California at Davis).

Antibodies: IE62 (Narayanan et al., Proc. Natl. Acad. Sci. USA, 2007, 104, 10835-40); HCF-1 (Kristie et al., J. Biol. Chem., 1995, 270, 4387-94); Normal rabbit IgG, H3K4-trimethyl, H3K9-monomethyl, H3K9-dimethyl, HP1γ, CoREST (Millipore/Upstate Biotechnologies, Lake Placid, N.Y.: 12-370, 05-745, 07-450, 05-690, 07-455, respectively); FLAG-M2, V5 (Sigma-Aldrich), HA (Roche), Tubulin, TBP, Sp1 (Santa Cruz Biotechnologies, Santa Cruz, Calif.: SC-1904, SC-273, SC-59, respectively); MLL1, Set1, RbBP5, BRAF35 (Bethyl Laboratories, Montgomery, Tex.: BL1408/1289, BL1193, BL766, A301-097A.1, respectively); Histone H3, LSD1, H3K9-trimethyl, HDAC1, H3K9-monomethyl, H3K9-dimethyl (Abcam, Cambridge, Mass.: ab1791, ab17721-ChIP/ab37165-Western, ab8898, ab7028, ab9045, ab1220, respectively); ICP0, ICP27, ICP4 (Goodwin Institute, Plantation, Fla.: GICR1112, GICR1113, and GICR1101, respectively); ICP8 (provided by William Ruyechan, University at Buffalo, SUNY), and Neurofilament 200 (Sigma N012).

Example 1

This example demonstrates the role of histone methylation in herpesvirus gene expression.

Methods

Reporter assays: The VZV model IE promoter-reporter (pIE62P-61), IE62 expression plasmid (pCMV-IE62), and luciferase reporter assays have been described previously (Narayanan et al., Proc. Natl. Acad. Sci. USA, 2007, 104, 10835-40). The VZV model IE promoter-luciferase reporter contained the minimal promoter sequences required for IE62 mediated induction (−61 to +73 relative to the IE62 transcription initiation site) in pGL3Basic (pIE62P-61). pCMV-IE62 expresses the IE62 activator under control of the CMV IE promoter (Narayanan et al. J. Biol. Chem., 2005, 280, 1369-75). The HSV IE promoter-luciferase reporter contained the promoter sequences for VP16 mediated induction (−171 to +57 relative to the ICP0 transcription initiation site) in pGL4.18 (pICP0-171). Luciferase reporter activity was measured and analyzed 24 hrs later as described using the Dual-Luciferase Assay Kit (Promega, Madison, Wis.) in a Berthold luminometer (Narayanan et al., Proc. Natl. Acad. Sci. USA, 2007, 104, 10835-40). All activity units were normalized by protein concentration and the activity of the internal control vector.

Chromatin immunoprecipitations (ChIP) from extracts of control, HCF-1 depleted, and LSD1 depleted cells were done essentially as described (Narayanan et al., Proc. Natl. Acad. Sci. USA, 2007, 104, 10835-40). Recovered DNA was subjected to semi-quantitative PCR with dilutions of input DNA to insure linearity using PCR Supermix (Invitrogen, Carlsbad, Calif.) with the following conditions: 95° C. for 2 min followed by 20 cycles of 95° C. for 30 sec; 59° C. for 30 sec; 72° C. for 30 sec. The signal intensities of individual bands, resolved in ethidium bromide agarose gels, were calculated as a percentage of the intensity of the input extract after subtraction of the appropriate background antibody controls. Signal intensities of resolved bands were quantitated using a Kodak 4000MM Image Station.

Samples also were analyzed, in triplicate, by qPCR using ABI Sybr Green PCR Master Mix. For qPCR, samples were run on a ABI PRISM 7900HT with the following conditions: 95° C. for 10 min followed by 40 cycles of 95° C. for 15 sec; 57° C. for 15 sec; 72° C. for 30 sec. Results were analyzed using ABI SDS 2.3 software.

Primer sets for ChIP were as follows:

```
VZV IE model promoter
                                     (SEQ ID NO: 1)
5'R            ACTAGCAAAATAGGCTGTCCCCAG
                                     (SEQ ID NO: 2)
3'R            CCTTTCTTTATGTTTTTGGCGTC VZV IE62 promoter (genomic)
                                     (SEQ ID NO: 3)
5'P            GAAATAGACACCGGGCGTACATC
                                     (SEQ ID NO: 4)
3'P            GAATTTAGACGTACCCGAGTTTTCC VZV IE62 coding (genomic)
                                     (SEQ ID NO: 5)
5'C            GTTGCAGACGATCATGTGGTTTC
                                     (SEQ ID NO: 6)
3'C            GTCGCGAGGGTGCTCTCG HSV ICP0 promoter (distal)
                                     (SEQ ID NO: 7)
P1-5'          CGCGGGTCGCTCAATGAAC
                                     (SEQ ID NO: 8)
P1-3'          GCCCGGCCCCCGATT HSV ICP0 promoter (proximal)
                                     (SEQ ID NO: 9)
P15-5'         CCCTGGCCCGACAGTCTG
                                     (SEQ ID NO: 10)
P15-3'         CAGGCCGGCGGGTACTC GAPDH-pr
                                     (SEQ ID NO: 23)
GPr-5'         CGGACTGCAGCCCTCCC
                                     (SEQ ID NO: 24)
GPr-3'         CCTTCCCAGTTTCCGACTGTCC Actin-pr
                                     (SEQ ID NO: 21)
APr-F          TGGCTCAGCTTTTTGGATTC
                                     (SEQ ID NO: 22)
APr-R          GGGAGGATTGGAGAAGCAGT
```

Results

A reporter system in which HeLa cells were transfected with a model VZV IE promoter-reporter was utilized. The state of histone H3K4 and H3K9 methylation was assessed by chromatin immunoprecipitation/qPCR assays in the presence and absence of the VZV IE activator (IE62). In the absence of the activator, repressive H3K9 methylation accumulated on the promoter. In the presence of the activator, H3K9 methylation was reduced and positive H3K4 trimethylation was enhanced.

These data suggest that, in addition to the Set1/MLL1 H3K4 methyl-transferase, an H3K9 demethylase is likely required in order to remove these repressive marks for activation of transcription.

Example 2

This example demonstrates the roles of HCF-1, Set-1 and LSD1 in viral IE gene transcription.

Methods

The methods of Example 1 were followed. In addition, for LSD1 depletion, $4 \times 10^4$ cells were transfected with 1 µg control RNAi, LSD-1, or LSD-2 shRNA constructs (Origene TR20003, TI365146 (GATACTGTGCTTGTCCAC-CGAGTTCACAG (SEQ ID NO: 37), and TI365147 (GGATTTGGCAACCTTAACAAGGTGGTGTT (SEQ ID NO: 38)), respectively) using Fugene 6 according to the manufacturer's recommendations (Roche Applied Science, Indianapolis, Ind.). 48 hours post transfection, the cells were cotransfected with 100 ng reporter construct, 0.1 ng RL-CMV internal control, and increasing amounts of pCMV-IE62. Luciferase reporter activity was measured and analyzed 24 hours later as described in Example 1.

Results

In concert with HCF-1 and Set1, LSD1 also was recruited to the model IE promoter. Reduction in the levels of LSD1 using two distinct LSD1-RNAi(s) resulted in reduced induction of the IE reporter, demonstrating that LSD1 was important for IE62 mediated transcriptional activation. In a similar manner, depletion of LSD1 reduced the induction of the induction of an HSV-1 IE reporter. Transfection of a construct expressing LSD1 stimulated the reporter, while that expressing an LSD1 mutant had no significant impact.

Example 3

This example demonstrates the recruitment of LSD1 is dependent upon the coactivator HCF-1.

Methods

The methods of Example 1 were followed. In addition, HSV (strain 17) infections were done by exposing uninfected cells to HSV infected cell lysates in DMEM medium containing 1% fetal bovine serum. At 1 hr post infection, the medium was replaced with DMEM containing 10% serum and incubation was continued. VZV infections were done by directly overlaying VZV-infected MeWo cells unto naïve BS-C-1 cells and then using these infected BS-C-1 cells to overlay new BS-C-1 naïve cells. Depletion of HCF-1 was accomplished using anti-HCF-1 RNAi constructs. For HCF-1 depletion, HCF-1 RNAi was used as described in Narayanan et al., J. Biol. Chem., 2006, 280, 1369-1375.

Results

In HCF-1 depleted cells, H3K4 trimethylation of the model promoter was reduced (7-fold) while H3K9 methylation was enhanced 8-9-fold, correlating with a decrease in the promoter occupancy by Set1 and LSD1. In contrast, occupancy of the DNA binding viral IE activator (IE62) is HCF-1 independent in this system and was equivalent in both HCF-1(−) and HCF-1(+) cells.

Cells were infected with VZV and the chromatin modification status and protein occupancy was assessed for the viral IE promoters in HCF-1 depleted and control cells. In these experiments, HCF-1 was only partially depleted (52%) to prevent impacts on cell cycle progression and changes in the levels of the viral IE62 activator. In control cells, promoter occupancy by IE62, HCF-1, Set1, MLL1, and LSD1 were all substantial, in contrast to occupancy of control coding sequences. Binding of these proteins correlated with high levels of H3K4 trimethylation and near background levels of repressive H3K9 methylation. Equivalent results were also obtained in analysis of the promoters of the HSV IE genes. However, in cells partially depleted for HCF-1, occupancy by Set1 and LSD1 decreased with a correlating decrease in the levels of H3K4 trimethylation and increase in the levels of the repressive H3K9 methylation.

These data indicate that the HCF-1 dependent recruitment of Set1 and LSD1 was important to remove the repressive H3K9 chromatin marks from the viral promoter and promote H3K4 methylation.

Example 4

This example demonstrates the significance of the recruitment of LSD1 to enable productive VZV infection.

Methods

Viral infections were performed as described in Example 3. Depletion of LSD1 was accomplished using a MCF7 doxycycline inducible LSD1-RNAi cell line. Expression of the LSD1 RNAi was induced for 96 hours prior to infection of the depleted cells with VZV.

qRT-PCR: Oligo dT primed cDNA was produced from total RNA using RNAqueous-4PCR and RETROscript (Ambion, Austin, Tex.) according to the manufacturer's recommendations. cDNA was quantitated by qPCR.

Primer sets for RT-PCR were as follows:

```
ICP0
                                           (SEQ ID NO: 11)
F          CCCACTATCAGGTACACCAGCTT
                                           (SEQ ID NO: 12)
R          CTGCGCTGCGACACCTT

IE62
                                           (SEQ ID NO: 13)
F          TGGACGAGGCGGCACATAG
                                           (SEQ ID NO: 14)
R          AGGGCGTGGCGGCAAAACAC

ICP27
                                           (SEQ ID NO: 15)
F          GCATCCTTCGTGTTTGTCATTCTG
                                           (SEQ ID NO: 16)
R          GCATCTTCTCTCCGACCCCG s15
                                           (SEQ ID NO: 17)
F          TTCCGCAAGTTCACCTACC
                                           (SEQ ID NO: 18)
R          CGGGCCGGCCATGCTTTACG

ICP4
                                           (SEQ ID NO: 19)
F          TGCTGCTGCTGTCCACGC
                                           (SEQ ID NO: 20)
R          CGGTGTTGACCACGATGAGCC

Actin
                                           (SEQ ID NO: 21)
F          TGGCTCAGCTTTTTGGATTC
                                           (SEQ ID NO: 22)
R          GGGAGGATTGGAGAAGCAGT Sp1
                                           (SEQ ID NO: 25)
F          TCAGAACCCACAAGCCCAAAC
                                           (SEQ ID NO: 26)
R          TGCCAGCAGGAATGGAAGC
```

```
                              -continued
TBP
                                                   (SEQ ID NOT: 27)
F            TGACCCCCATCACTCCTGC
                                                   (SEQ ID NO: 28)
R            CGTGGTTCGTGGCTCTCTTATC
```

For the detection of viral IE and cellular mRNAs post explant, 8 ganglia from HSV latently infected or mock infected Balb/c mice were explanted in the presence of DMSO, 100 μM acyclovir, or 2 mM TCP for the indicated times. cDNAs were prepared from total RNA and amplified by qPCR (cellular Sp1 and TBP controls) or nested PCR (viral IE). Primer sets for the nested RT-PCR were as follows:

```
ICP4 Primary
                                                   (SEQ ID NO: 29)
F            GCGAGCAGCCCCAGAAACTC
                                                   (SEQ ID NO: 30)
R            ACGACGATAACCCCCACCC ICP4 Secondary/Nested
                                                   (SEQ ID NO: 31)
F            GGACAGCAGCAGCACGCC
                                                   (SEQ ID NO: 32)
R            ATCCCCGACCCCGAGGACG ICP27 Primary
                                                   (SEQ ID NO: 33)
F            CCCCAGGACCCCATTATCG
                                                   (SEQ ID NO: 34)
R            TTCTCTCCGACCCCGACACCAAGG ICP27 Secondary/Nested
                                                   (SEQ ID NO: 35)
F            GCTGGATAACCTCGCCACG
                                                   (SEQ ID NO: 36)
R            CAGAATGACAAACACGAAGGATGC
``` cDNA samples were normalized to one another according to the level of cellular control Sp1 mRNA. To insure linearity and sensitivity of nested PCR reactions, samples were amplified in parallel with dilutions of cDNA prepared from 3T3 cells infected with HSV at $6.4 \times 10^{-5}$ pfu/cell for 4 hrs. PCR products were resolved in agarose gels and quantitated using Kodak Image Station 4000MM Digital Imaging System.

Coimmunoprecipitations: $2.5 \times 10^6$ HEK293 cells were transfected with 9.6 ug pHA-LSD and 14.4 ug pHCF-FLAG or pHCF-V5 expression plasmids using Lipofectamine 2000 (Invitrogen, Carlsbad, Calif.). Forty-eight hours later, nuclear extracts were incubated with FLAG-M2 agarose beads (Sigma, St. Louis, Mo.) at 4° C. for 1 hr in NP-40 buffer (50 mM Tris pH 7.5, 150 mM NaCl, 0.1% NP-40, 5% glycerol, 1 mM NaF, 10 mM β-glycerophosphate, 0.1 mM $Na_3VO_4$, Complete protease inhibitor). For endogenous coimmunoprecipitations, antibodies were prebound to Protein G Dynabeads and incubated with HeLa cell nuclear extracts in NP-40 buffer overnight. Immunoprecipitates were washed 5 times with binding buffer, eluted in SDS sample buffer, and resolved in 4-20% Tris-Glycine gels. Western Blots of resolved extracts and immunoprecipitates were developed using Pierce SuperSignal West Dura.

Results

The levels of LSD1 and VZV IE protein and mRNAs were determined by Western blot and qRT-PCR, respectively. Depletion of 60% of the cellular LSD1 reduced the levels of the viral IE protein by 66% and mRNA by 78%. Similar impacts on the expression of the HSV IE proteins also were seen in LSD1 depletion experiments and significant levels of viral IE gene expression was recovered in LSD1 depleted cells by exogenous expression of wild-type LSD1, but not by expression of a LSD1 catalytic mutant or a mutant lacking the amine oxidase domain. Depletion of LSD1 resulted in an increased accumulation of nucleosomes bearing repressive H3K9 methylation on the viral IE promoters.

To determine whether recruitment of LSD1 was based on an interaction with HCF-1, immunoprecipitates of endogenous LSD1 were probed for HCF-1. Immunoprecipitation with either Set1- or LSD1-specific antibodies resulted in efficient coimmunoprecipitation of HCF-1.

As HCF-1 is a component of the Set1 and MLL1 histone H3-lysine 4 methyl-transferase complexes (HMTs), whether LSD1 was associated with the HCF-1 HMT complex or was present in a distinct HCF-1 complex was determined by probing HCF-1 and LSD1 immunoprecipitates for RbBP5, a common core subunit of the Set1 and MLL HMT complexes. Both proteins coimmunoprecipitated the HMT core subunit, suggesting that LSD1 was associated with the HCF-1 HMT complex.

To further characterize the HCF-1/LSD1 complex, immunoprecipitates from cells expressing epitope tagged HCF-1 and LSD1 were probed for cofactors associated with the repressive CoREST/LSD1 complex. Such factors were present in the LSD1 immunoprecipitate but were absent from the activating HCF-1/LSD1 complex.

Based on these data, HCF-1 couples the demethylase LSD1 with the Set1/MLL1 methyltransferase complex, providing both specificities required to activate the expression of transcriptionally repressed genes (IE gene transcription).

To further define the requirement of HCF-1 in viral reactivation, chromatin immunoprecipitation assays were used to demonstrate that HCF-1 is rapidly recruited to the IE promoter-enhancer domains of latent viral genomes (e.g., HSV-1) during the initial stages of reactivation. In sensory neurons, recruitment of HCF-1 was detected as early as 1 hr post induction of reactivation and occupancy increased by 4 hrs post induction. This time course correlates well with the nuclear transport of HCF-1, where the number of neurons exhibiting nuclear localization increases over the course of 6 hrs post stimulation. Additionally, HCF-1 occupancy of viral IE promoter domains correlated with the occupancy by RNAPII and accumulation of viral IE mRNAs. The recruitment of HCF-1 is correlated with the association of RNAPII and the detection of IE mRNA.

These data support a model in which HCF-1 is involved in both the initiation of lytic infection and the reactivation of HSV-1 from latency.

Example 5

This example demonstrates MAOI inhibition of LSD1 and the α-herpesvirus lytic cycle.

Methods

For treatment with MAOIs, cells were pretreated with the indicated concentration of drug for 4-5 hrs prior to infection and maintained throughout infection. Pargyline (p-8013) and Tranylcypromine (p-8511) were obtained from Sigma (St. Louis, Mo.).

Cell infections: For HSV, cells were infected with 0.1 plaque forming units (PFU) of HSV per cell for 24 hrs in the presence of 2 mM Tranylcypromine (TCP) or control DMSO. The resulting viral yields were determined by titer of infected cell lysates on Vero cell monolayers. VZV infections were performed as in Example 3.

Results

Figure 2:
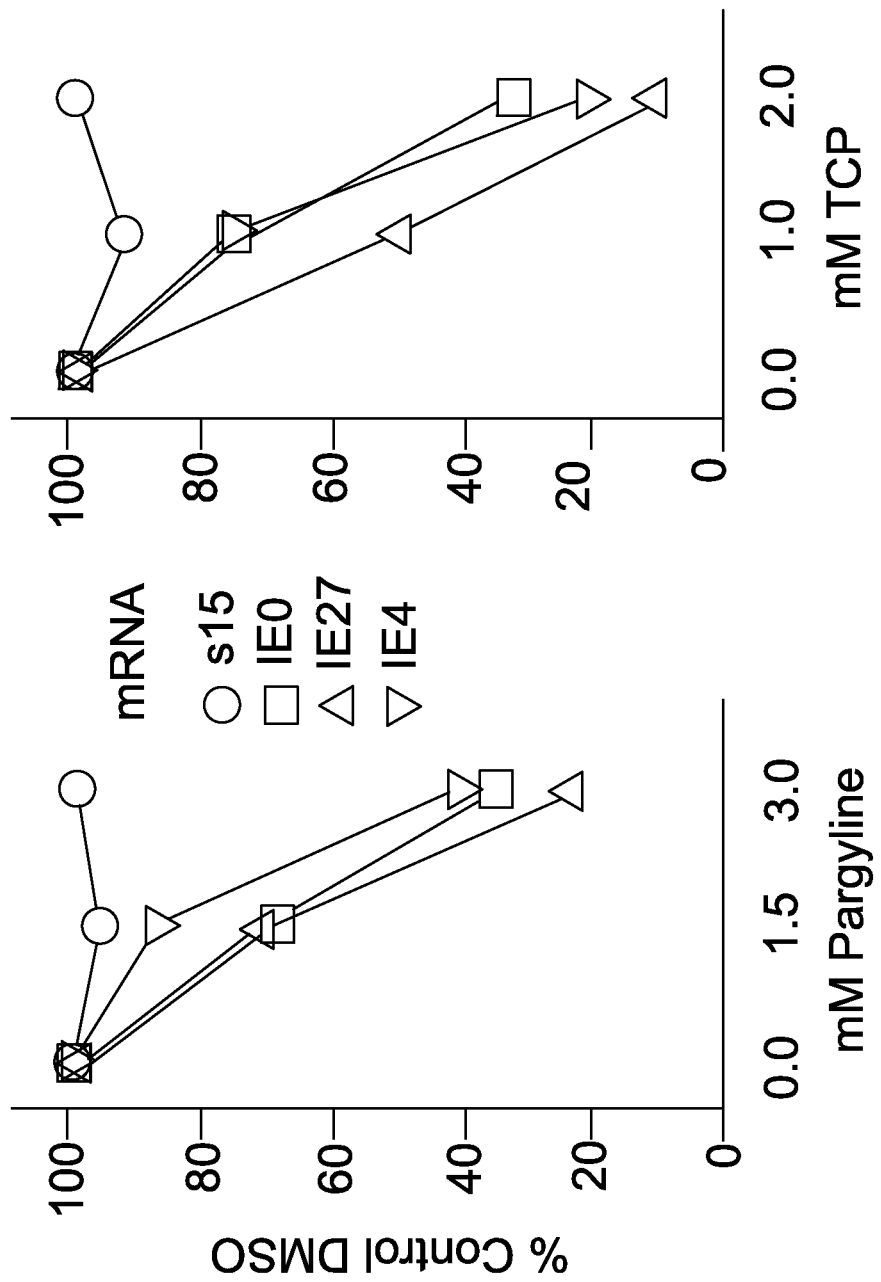
FIG. 2 shows treatment of herpes simplex virus (HSV)-infected cells with monoamine oxidase inhibitors resulted in a dose dependent decrease in viral mRNA and IE proteins. These data were generated using qRT-PCR analyses of mRNA levels of HSV IE genes and control s15 in cells treated with selected concentrations of Pargyline or Tranylcypromine (TCP). The mRNA levels are graphically represented as the percent of mRNA levels in control DMSO treated cells.

The impact of the MAOIs Pargyline and TCP on VZV and HSV infection was investigated. In each case, treatment with the inhibitor resulted in a dose dependent decrease in viral mRNA and IE proteins (FIGS. 1 and 2) with no impact on cellular protein controls and no significant cellular toxicity. In addition, viral yields from cells infected with HSV in the presence of TCP were reduced nearly 1000-fold. These results suggested that inhibition of LSD1 demethylase activity with MAOIs results in the accumulation of repressive chromatin on the viral IE promoters, similar to that observed in LSD1 RNAi-mediated depletions (see Example 2) In the presence of TCP or Pargyline, nucleosomes bearing repressive marks accumulated on the viral IE promoters as detected by the increase in histone H3 and H3K9 methylation. These results support a model whereby LSD1 is required to prevent accumulation of repressive H3K9 methylation, thereby allowing initiation of productive infection by both α-herpesviruses.

In the presence of TCP, a high level of nucleosomes bearing repressive marks accumulated on the viral IE promoters as detected by the substantial increase in histone H3 and H3K9 trimethylation. In contrast, the level of H3K4 trimethylation did not significantly change, even though the level of assembled chromatin increased. It is important to note, that even in untreated cells, repressive H3K9 methylation is detected as early as 30 minutes post infection and these marks decreased over time as HCF-1 dependent complexes were recruited to the viral IE promoters.

In addition to the increase in mono- and di-methyl H3K9, inhibition of LSD1 ultimately resulted in an increase in the level of repressive H3K9-trimethylation and promoter occupancy by the heterochromatin protein 1 (HP1). As LSD1 only removes mono- and di-methyl modifications, the increase in H3K9 trimethyl marks in the absence of LSD1 could reflect the increased levels of dimethyl substrates that accumulate during chromatin assembly on the viral genome. Even in the presence of LSD1, H3K9 trimethyl marks are readily detected on the viral IE promoters during the early stages of infection, suggesting that additional H3K9 demethylase(s) of the Jmjd family could be required in conjunction with LSD1 to promote viral IE gene expression. The requirement for LSD1 to promote viral IE expression identifies it as a target for inhibition of α-herpesviruses lytic infection.

These data show that MAOIs inhibit LSD1 and the α-herpesvirus lytic cycle.

Example 6

This example demonstrates that MAOIs used to inhibit LSD1 and the α-herpesvirus lytic cycle also inhibit the α-herpesvirus re-activation cycle.

Methods

Latently infected mice and trigeminal ganglia: Balb/c mice were infected with $5 \times 10^5$ PFU HSV-1 (strain 17) per eye after corneal scarification. Latently infected mice were sacrificed 30 days post clearance of the primary infection and trigeminal ganglia were rapidly explanted into culture in the presence or absence of TCP or control (DMSO or acyclovir). Post explant incubation as indicated, the ganglia were homogenized and briefly sonicated. The reactivated viral yield of each ganglia was determined by titering the clarified supernatant on Vero cells.

Statistical analyses: Statistical comparisons were made using Wilcoxon signed rank test (paired ganglia) with a statistical significance of <0.05; Kruskal-Wallis test with post hoc Dunn's multiple comparison test (drug titration and reversal) with a statistical significance of <0.025; Mann-Whitney U test with Dunn's post hoc adjustment (non-paired ganglia time course) with a statistical significance of <0.025; or Fischer's Exact Test with a statistical significance of <0.05. Analyses were made using Prism (V5.0a) and are expressed as the mean+/−s.e.m.

Non-paired ganglia time course statistic analysis: Comparisons were made between control (DMSO) and TCP treated ganglia on day 2 and day 4 post explant. Each comparison utilized a one-sided Mann-Whitney U test followed by application of the Dunn's post hoc adjustment to the p-values. Significant differences were found between DMSO and TCP on day 2 (p=0.0043) and on day 4 (p=0.0011). Both of these differences are still significant after applying the Dunn's adjustment as both are less than the alpha level (α=0.025). The Mann-Whitney tests used an exact p-value for small sample sizes. n=6 for each sample set.

Paired ganglia statistical analysis: Each data point was the result of a single ganglia divided and treated in the presence and absence of TCP. Therefore, a Wilcoxon signed rank test was used to assess differences between each treated and untreated sample. The significant difference was p=0.0002. This test used an exact p-value for small sample sizes with an α level of 0.05. n=16 for each sample set.

TCP titration statistical analysis: To determine at what concentration TCP that would produce a significant reduction in viral load, a Kruskal-Wallis (K-W) test with Dunn's post hoc comparison was used. The K-W test was appropriate due to the comparison of five samples of data that are not normally distributed. Significant differences were found between the five groups (p=0.0007, K-W=19.39). To determine which groups are significantly different, a Dunn's post hoc comparison was done. Assessment of each concentration of TCP as compared to the control (DMSO) demonstrated that 1.0, 1.5, and 2.0 mM data sets showed significant differences (p<0.05) while 0.5 mM did not. Comparing each concentration of TCP against the next higher concentration demonstrated that 1.0 mM was significantly better at repressing viral yields than 0.5 mM. No significant difference was found between 1.0 and 1.5 or 1.5 and 2.0 mM data sets. n=5 for control, 0.5, 1.0, and 2.0 mM; n=6 for 1.0 mM.

TCP reversal statistical analysis: Viral yields from ganglia treated without TCP for 2 days, treated with TCP for 2 days, or treated with TCP for 2 days followed by incubation in the absence of drug for 3 days were compared using the K-W test followed by Dunn's post hoc comparisons. The K-W test was appropriate due to the comparison of three samples of data that are not nominally distributed. Significant differences were found between the groups (p=0.0007, K-W=10.3). A significant difference was demonstrated between the TCP and TCP-R data sets using Dunn's post hoc comparison (α=0.025). n=4 for TCP; n=6 for TCP-R.

Immunofluorescence statistical analysis: Trigeminal ganglia (16 DMSO/Control, 15 acyclovir, and 15 TCP) were fixed at 48 hours post explants. Serial sections representing the entire ganglia were stained and scored by confocal microscopy. Ganglia were scored as HSV+ when any section exhibited ICP8 specific staining. Of the 15 TCP treated ganglia, only one section of one ganglia exhibited a single ICP8+ neuron. A Fischer's Exact Test demonstrated that there was significant difference between DMSO, acyclovir, and TCP treated ganglia (p=0.00002). The Odds Ratio indicated that the odds of viral reactivation were 1.4444 times higher for the DMSO treated samples as compared to the acyclovir treated samples, 60.6667 times higher for the DMSO treated samples as compared to the TCP treated samples, and 42.0000 times higher for the acyclovir treated samples as compared to the TCP treated samples.

Results

Figure 3:
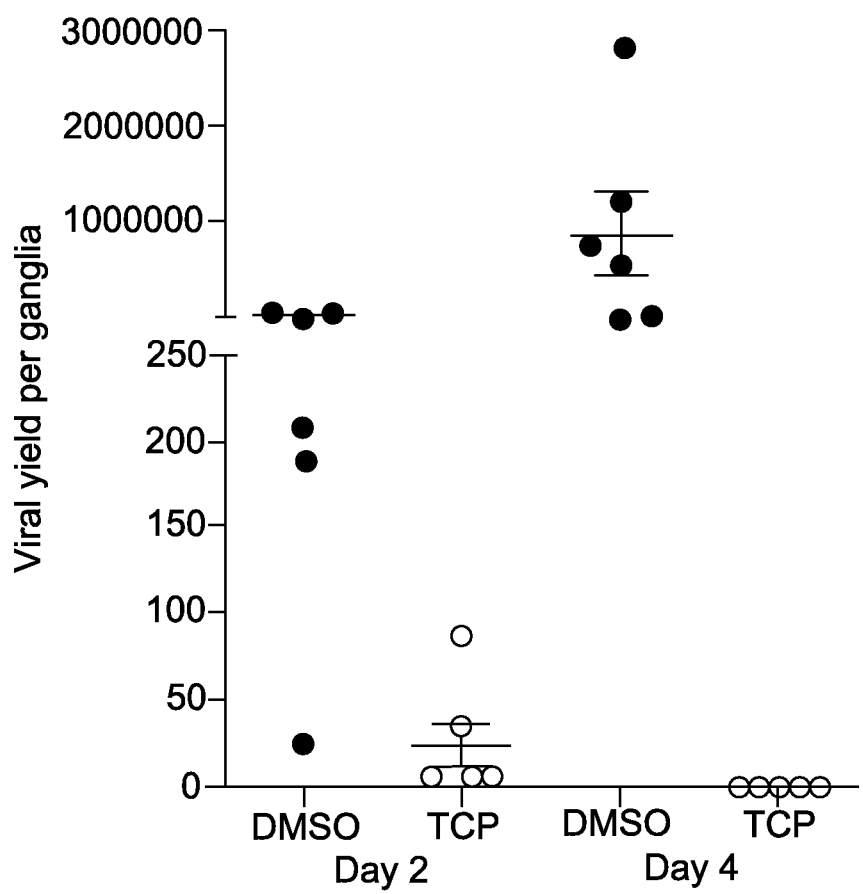
FIG. 3 shows a decrease in viral yield in HSV latently infected mice upon administration of TCP. The data are viral yields from a time course of explanted trigeminal ganglia of latently infected mice in the presence or absence of 2 mM TCP for 2 days or 4 days; n=6 for each sample set. In the absence of TCP, DMSO was used as the control treatment vehicle.

In addition to the lytic cycle, α-herpesviruses establish persistent latent infections and cycles of reactivation in sensory neurons that are characterized by alterations in chromatin modifications on the viral IE promoters. HSV latently infected mice were induced to reactivate virus by tissue explant of the trigeminal sensory ganglia (TGs) for 2 or 4 days in the presence and absence of the MAOI TCP (FIG. 3). Strikingly, TCP significantly reduced the reactivation of HSV-1 as compared to the control treated ganglia (p values=0.0043 and 0.0011 for days 2 and 4, respectively). Similar results were observed for the MAOI selegiline (data not shown).

Figure 4:
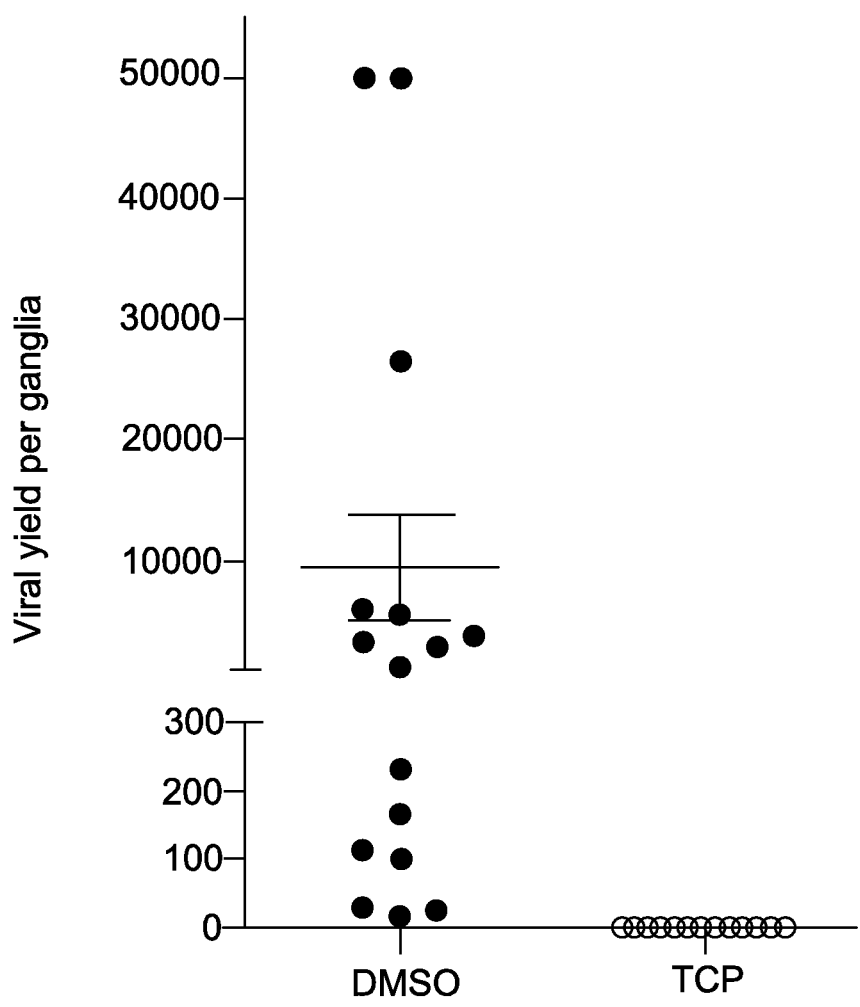
FIG. 4 shows a decrease in viral yield in HSV latently infected mice upon administration of TCP using a direct paired analysis in which each half of a latently infected ganglia was explanted in the presence and absence of TCP. The data are viral yield from paired explanted ganglia of latently infected mice in the presence or absence of 2 mM TCP for 2 days; n=16 for each sample set. In the absence of TCP, DMSO was used as the control treatment vehicle.
Figure 5:
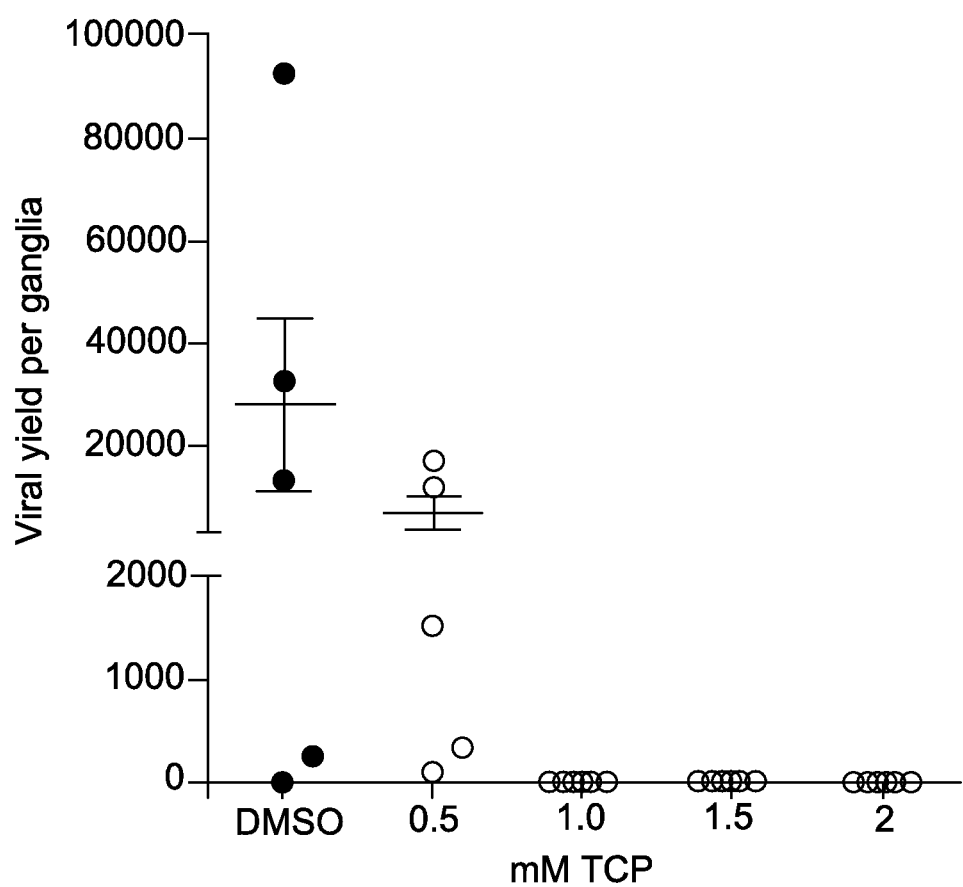
FIG. 5 shows inhibition of HSV reactivation from latency at various levels of TCP using viral yield from explanted trigeminal ganglia of latently infected mice in the presence or absence of various concentrations of TCP for 2 days. In the absence of TCP, DMSO was used as the control treatment vehicle.
Figure 6:
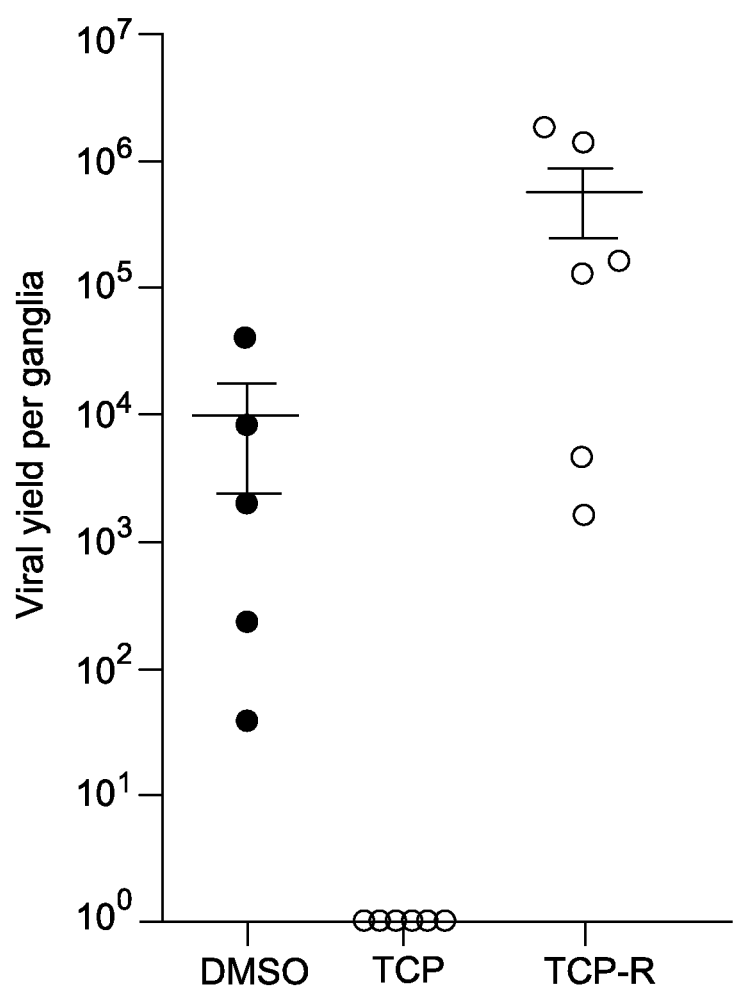
FIG. 6 shows that reversal of TCP inhibition results in HSV reactivation. Viral yields from explanted trigeminal ganglia of latently infected mice are shown in the absence or presence of 2 mM TCP for 2 days. In the absence of TCP, DMSO was used as the control treatment vehicle. A portion of the TCP treated samples were then incubated in the absence of drug (DMSO) for 3 days (TCP-R).

Due to the potential variance in the viral load of individual animals, these studies were repeated using a direct paired analysis in which each half of a latently infected ganglia was explanted in the presence and absence of TCP (FIG. 4). These results confirmed the significance of TCP inhibition of viral reactivation (p value=0.0002). While the level of TCP used in these tissue explant experiments was equivalent to that determined to inhibit LSD1 in cell culture, titration of the drug suggested that lower levels also were effective (FIG. 5). To rule out the impacts of potential TCP toxicity, latently infected ganglia were explanted in the presence of TCP for 2 days followed by incubation in the absence of drug for 3 days. The high level of viral reactivation following drug removal indicated that toxicity was not responsible for the suppression of viral reactivation (FIG. 6).

These viral yield studies suggested that inhibition of LSD1 with MAOIs prevented the initiation of viral reactivation in the sensory neurons. However, it remained formally possible that TCP inhibited lytic spread of the virus in the ganglia but not the initial reactivation events. Therefore, latently infected ganglia were explanted in the presence of DMSO (control vector), acyclovir (to prevent viral DNA replication and spread), or TCP for 48 hrs. Ganglia were fixed and sections were probed with antibodies to HSV ICP8, the viral-encoded single stranded binding protein. In ganglia explanted in DMSO, clusters of ICP8 (+) neurons were detected throughout multiple sections in 13 of 16 ganglia, representing initiating neurons as well as infected neurons and support cells resulting from lytic spread in the ganglia. In the presence of acyclovir, distinct ICP8 (+) neurons were clearly detected in several sections in 9 of 12 ganglia, representing the primary neurons undergoing viral reactivation. Strikingly, in the presence of TCP, only a single ICP8 (+) neuron was detected in 1 of 15 ganglia explanted, clearly demonstrating that TCP inhibited viral reactivation rather than inhibiting lytic spread of the infection through the ganglia (p value=0.00002).

As an additional approach to demonstrating TCP inhibition of HSV reactivation, cDNA was prepared from RNA isolated from paired latently infected ganglia explanted in the presence of acyclovir or TCP for 12 hrs and analyzed by nested PCR for the detection of a representative HSV IE mRNA (ICP27). In the presence of control acyclovir, ICP27 mRNA was readily detected at a level comparable to that in control cDNA produced from 3T3 cells infected with HSV. In contrast, in ganglia explanted in the presence of TCP, the level of ICP27 mRNA was not significantly above that of background controls (reverse transcriptase). Similarly, viral IE mRNAs (ICP4 and ICP27) were clearly detected in ganglia explanted for 7 hrs in the absence but not the presence of TCP.

The data supports the conclusion that MAOIs, such as TCP, inhibit viral IE gene expression and, consequently, reactivation of HSV from latency.

Example 7

This example demonstrates repression of adenovirus E1A expression by the MAO inhibitor TCP.

Methods

Viral infection and treatment with TCP: HeLa cells ($2 \times 10^6$) were treated with control DMSO (D) or 2 mM Tranylcypromine (T) for 5 hours prior to infection with various amounts of Adenovirus Type 5 ($1.2 \times 10^8$, $2.3 \times 10^8$, and $4.5 \times 10^8$ NAS IU) for 2 or 4 hours. Equal amounts of infected cell lysates were resolved by SDS-PAGE and Western blotted with anti-E1A, anti-LSD1, and anti-β tubulin antibodies. HEK293 and uninfected HeLa cell lysates represented E1A positive and negative controls.

Results

Similar to the inhibition of the expression of the IE genes of the α-herpesviruses (HSV and VZV), Tranylcypromine also inhibits the expression of the adenovirus IE protein E1A. In contrast no significant impact on the levels of the controls LSD1 and β-Tubulin are seen.

Example 8

This Example demonstrates dose-dependent repression of adenovirus E1A expression by TCP.

Methods

HeLa cells ($2 \times 10^6$) were treated with control DMSO (D) or various concentrations of Tranylcypromine (TCP) for 5 hours prior to infection with $2.3 \times 10^9$ NAS IU of adenovirus Type 5 for 2 hours. Equal amounts of infected cell lysates were resolved by SDS-PAGE and Western blotted with anti-E1A, anti-β Tubulin, and anti-TBP antibodies.

Results

Figure 7:
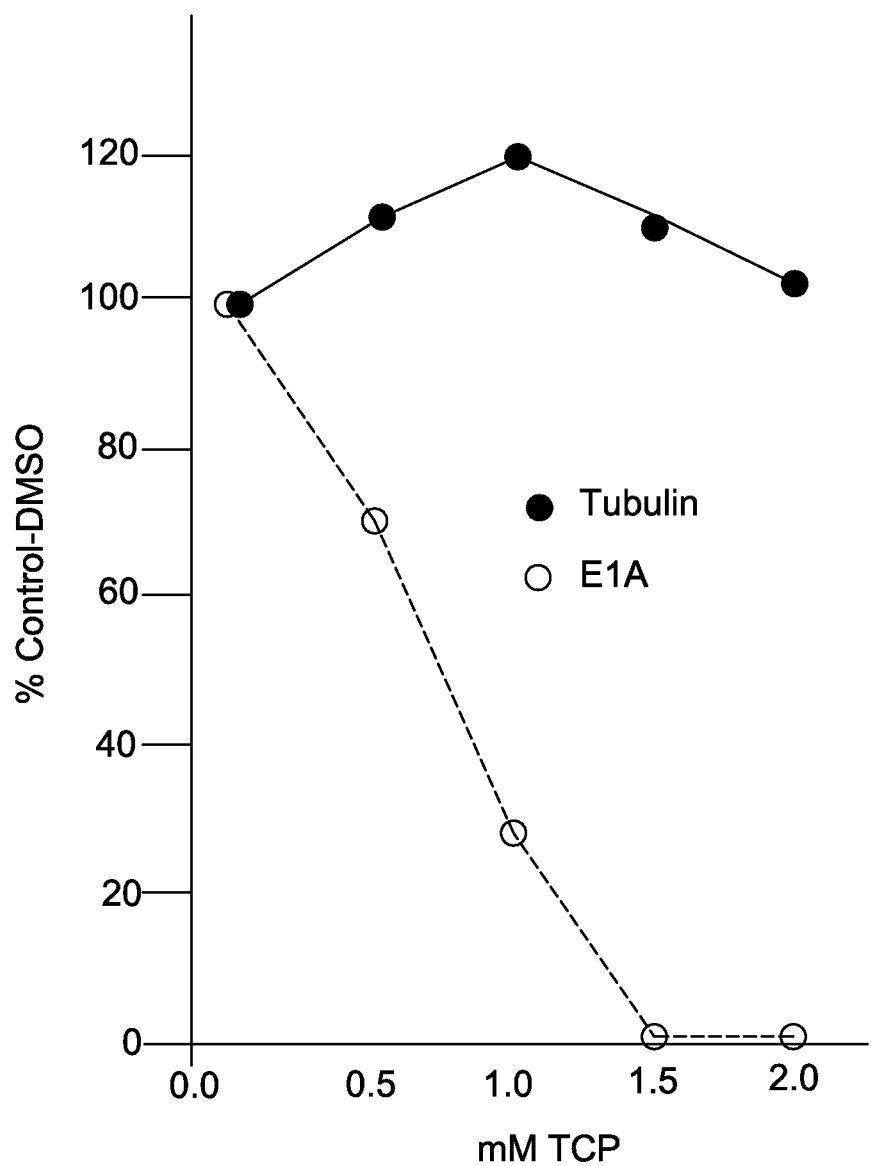
FIG. 7 shows dose-dependent repression of adenovirus E1A expression by TCP, whereas the expression of the control tubulin is largely unaffected.

Inhibition of expression of the adenovirus Immediate Early protein E1A by TCP is seen in the same concentration range as demonstrated for the inhibition of the expression of the α-herpesvirus immediate early proteins (FIG. 7). In contrast, no significant impact was seen on the levels of the control TBP and β-Tubulin proteins.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of treating a herpesvirus or adenovirus viral infection of a host, comprising (a) detecting an immediate early (IE) gene expression level of the viral infection, (b) administering to the host an effective amount of an inhibitor of the protein LSD1, wherein the inhibitor is a non-monoamine oxidase inhibitor, and (c) detecting the IE gene expression level after administration of the inhibitor, wherein the viral infection is treated when the IE gene expression level is lower after administration of the inhibitor than before administration of the inhibitor.

2. The method of claim 1, wherein the inhibitor is an RNA interference inhibitor.

3. The method of claim 2, wherein the RNA interference inhibitor is GATACTGTGCTTGTCCACCGAGTTCACAG (SEQ ID NO: 37) or GGATTTGGCAACCT-TAACAAGGTGGTGTT (SEQ ID NO: 38) or the RNA equivalent thereof.

4. The method of claim 1, wherein the inhibitor is an antibody.

5. The method of claim 1, wherein the herpesvirus is herpes simplex virus type 1, herpes simplex virus type 2, varicella zoster virus, or cytomegalovirus.

6. The method of claim 1, wherein the adenovirus is adenovirus Type 1, 2, 3, 4, or 5.

7. A method of treating reactivation of a herpesvirus or adenovirus after latency in a host, comprising (a) detecting an immediate early (IE) gene expression level of the viral infection, (b) administering to the host an effective amount of an inhibitor of the protein LSD1, wherein the inhibitor is a non-monoamine oxidase inhibitor, and (c) detecting the IE gene expression level after administration of the inhibitor, wherein the viral infection is treated when the IE gene expression level is lower after administration of the inhibitor than before administration of the inhibitor.

8. The method of claim 7, wherein the inhibitor is an RNA interference inhibitor.

9. The method of claim 8, wherein the RNA interference inhibitor is GATACTGTGCTTGTCCACCGAGTTCACAG (SEQ ID NO: 37) or GGATTTGGCAACCT-TAACAAGGTGGTGTT (SEQ ID NO: 38) or the RNA equivalent thereof.

10. The method of claim 7, wherein the inhibitor is an antibody.

11. The method of claim 7, wherein the herpesvirus is herpes simplex virus type 1, herpes simplex virus type 2, varicella zoster virus, or cytomegalovirus.

12. The method of claim 7, wherein the adenovirus is adenovirus Type 1, 2, 3, 4, or 5.

13. A method of treating a herpesvirus or adenovirus viral infection in a mammal that has undergone, is undergoing, or will undergo an organ or tissue transplant, comprising (a) detecting an immediate early (IE) gene expression level of the viral infection, (b) administering to the host an effective amount of an inhibitor of the protein LSD1, wherein the inhibitor is a non-monoamine oxidase inhibitor, and (c) detecting the IE gene expression level after administration of the inhibitor, wherein the viral infection is treated when the IE gene expression level is lower after administration of the inhibitor than before administration of the inhibitor.

14. The method of claim 13, wherein the inhibitor is an RNA interference inhibitor.

15. The method of claim 14, wherein the RNA interference inhibitor is GATACTGTGCTTGTCCACCGAGT-TCACAG (SEQ ID NO: 37) or GGATTTGGCAACCT-TAACAAGGTGGTGTT (SEQ ID NO: 38) or the RNA equivalent thereof.

16. The method of claim 13, wherein the inhibitor is an antibody.

17. The method of claim 13, wherein the herpesvirus is herpes simplex virus type 1, herpes simplex virus type 2, varicella zoster virus, or cytomegalovirus.

18. The method of claim 13, wherein the adenovirus is adenovirus Type 1, 2, 3, 4, or 5.

* * * * *

SEQUENCE LISTING

```
<160> NUMBER OF SEQ ID NOS: 38

<210> SEQ ID NO 1
<211> LENGTH: 24
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: VZV IE model promoter forward primer (5R)

<400> SEQUENCE: 1
actagcaaaa taggctgtcc ccag                                          24

<210> SEQ ID NO 2
<211> LENGTH: 23
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: VZV IE model promoter reverse primer (3R)

<400> SEQUENCE: 2
cctttcttta tgtttttggc gtc                                           23

<210> SEQ ID NO 3
<211> LENGTH: 23
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: VZV genomic IE62 promoter forward primer (5P)

<400> SEQUENCE: 3
gaaatagaca ccgggcgtac atc                                           23

<210> SEQ ID NO 4
<211> LENGTH: 25
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: VZV genomic IE62 promoter reverse primer (3P)

<400> SEQUENCE: 4
gaatttagac gtacccgagt tttcc                                         25

<210> SEQ ID NO 5
<211> LENGTH: 23
<212> TYPE: DNA
<213> ORGANISM: Artificial Sequence
```

```
<220> FEATURE:
<223> OTHER INFORMATION: Synthetic Primer
<220> FEATURE:
<221> NAME/KEY: misc_feature
<223> OTHER INFORMATION: VZV genomic IE62 coding forward primer (5C)

<400> SEQUENCE: 5
gttgcagacg atcatgtggt ttc                                         23

<210> SEQ ID NO 6
<211> LENGTH: 18
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: VZV genomic IE62 coding reverse primer (3C)

<400> SEQUENCE: 6
gtcgcgaggg tgctctcg                                               18

<210> SEQ ID NO 7
<211> LENGTH: 19
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: HSV ICP0 promoter (distal) forward primer
      (P1-5)

<400> SEQUENCE: 7
cgcgggtcgc tcaatgaac                                              19

<210> SEQ ID NO 8
<211> LENGTH: 15
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: HSV ICP0 promoter (distal) reverse primer
      (P1-3)

<400> SEQUENCE: 8
gcccggcccc cgatt                                                  15

<210> SEQ ID NO 9
<211> LENGTH: 18
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: HSV ICP0 (proximal) forward primer (P15-5)

<400> SEQUENCE: 9
ccctggcccg acagtctg                                               18

<210> SEQ ID NO 10
<211> LENGTH: 17
<212> TYPE: DNA
<213> ORGANISM: Artificial Sequence
<220> FEATURE:
<223> OTHER INFORMATION: Synthetic Primer
```

```
<220> FEATURE:
<221> NAME/KEY: misc_feature
<223> OTHER INFORMATION: HSV ICP0 promoter (proximal) reverse primer
      (P15-3)

<400> SEQUENCE: 10
caggccggcg ggtactc                                                   17

<210> SEQ ID NO 11
<211> LENGTH: 23
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: ICP0 forward primer

<400> SEQUENCE: 11
cccactatca ggtacaccag ctt                                            23

<210> SEQ ID NO 12
<211> LENGTH: 17
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: ICP0 reverse primer

<400> SEQUENCE: 12
ctgcgctgcg acacctt                                                   17

<210> SEQ ID NO 13
<211> LENGTH: 19
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: IE62 forward primer

<400> SEQUENCE: 13
tggacgaggc ggcacatag                                                 19

<210> SEQ ID NO 14
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: IE62 reverse primer

<400> SEQUENCE: 14
agggcgtggc ggcaaaacac                                                20

<210> SEQ ID NO 15
<211> LENGTH: 24
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: ICP27 forward primer
```

-continued

```
<400> SEQUENCE: 15
gcatccttcg tgtttgtcat tctg                                          24

<210> SEQ ID NO 16
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: ICP27 reverse primer

<400> SEQUENCE: 16
gcatcttctc tccgaccccg                                               20

<210> SEQ ID NO 17
<211> LENGTH: 19
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: s15 forward primer

<400> SEQUENCE: 17
ttccgcaagt tcacctacc                                                19

<210> SEQ ID NO 18
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: s15 reverse primer

<400> SEQUENCE: 18
cgggccggcc atgctttacg                                               20

<210> SEQ ID NO 19
<211> LENGTH: 18
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: ICP4 forward primer

<400> SEQUENCE: 19
tgctgctgct gtccacgc                                                 18

<210> SEQ ID NO 20
<211> LENGTH: 21
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: ICP4 reverse primer

<400> SEQUENCE: 20
cggtgttgac cacgatgagc c                                             21
```

<210> SEQ ID NO 21
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: Actin forward primer

<400> SEQUENCE: 21
tggctcagct ttttggattc                                           20

<210> SEQ ID NO 22
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: Actin reverse primer

<400> SEQUENCE: 22
gggaggattg gagaagcagt                                           20

<210> SEQ ID NO 23
<211> LENGTH: 17
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: GADPH-pr forward primer (GPr-5)

<400> SEQUENCE: 23
cggactgcag ccctccc                                              17

<210> SEQ ID NO 24
<211> LENGTH: 22
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: GADPH-pr reverse primer (GPr-3)

<400> SEQUENCE: 24
ccttcccagt ttccgactgt cc                                        22

<210> SEQ ID NO 25
<211> LENGTH: 21
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: Sp1 forward primer

<400> SEQUENCE: 25
tcagaaccca caagcccaaa c                                         21

<210> SEQ ID NO 26
<211> LENGTH: 19

```
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: Sp1 reverse primer

<400> SEQUENCE: 26
tgccagcagg aatggaagc                                              19

<210> SEQ ID NO 27
<211> LENGTH: 19
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: TBP forward primer

<400> SEQUENCE: 27 tgaccccat cactcctgc                                               19

<210> SEQ ID NO 28
<211> LENGTH: 22
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: TBP reverse primer

<400> SEQUENCE: 28
cgtggttcgt ggctctctta tc                                          22

<210> SEQ ID NO 29
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: ICP4 primary forward primer

<400> SEQUENCE: 29
gcgagcagcc ccagaaactc                                             20

<210> SEQ ID NO 30
<211> LENGTH: 19
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: ICP4 primary reverse primer

<400> SEQUENCE: 30
acgacgataa ccccaccc                                               19

<210> SEQ ID NO 31
<211> LENGTH: 18
<212> TYPE: DNA
<213> ORGANISM: Artificial Sequence
<220> FEATURE:
<223> OTHER INFORMATION: Synthetic primre
```

```
<220> FEATURE:
<221> NAME/KEY: misc_feature
<223> OTHER INFORMATION: ICP4 secondary/nested forward primer

<400> SEQUENCE: 31
ggacagcagc agcacgcc                                                   18

<210> SEQ ID NO 32
<211> LENGTH: 19
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: ICP4 secondary/nested reverse primer

<400> SEQUENCE: 32
atccccgacc ccgaggacg                                                  19

<210> SEQ ID NO 33
<211> LENGTH: 19
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: ICP27 primary forward primer

<400> SEQUENCE: 33
ccccaggacc ccattatcg                                                  19

<210> SEQ ID NO 34
<211> LENGTH: 24
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: ICP27 primary reverse primer

<400> SEQUENCE: 34
ttctctccga ccccgacacc aagg                                            24

<210> SEQ ID NO 35
<211> LENGTH: 19
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: ICP27 secondary/nested forward primer

<400> SEQUENCE: 35
gctggataac ctcgccacg                                                  19

<210> SEQ ID NO 36
<211> LENGTH: 24
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: ICP27 secondary/nested reverse primer
```

```
<400> SEQUENCE: 36
cagaatgaca aacacgaagg atgc                                            24

<210> SEQ ID NO 37
<211> LENGTH: 29
<212> TYPE: DNA
<213> ORGANISM: Artificial Sequence
<220> FEATURE:
<223> OTHER INFORMATION: Synthetic

<400> SEQUENCE: 37
gatactgtgc ttgtccaccg agttcacag                                       29

<210> SEQ ID NO 38
<211> LENGTH: 29
<212> TYPE: DNA
<213> ORGANISM: Artificial Sequence
<220> FEATURE:
<223> OTHER INFORMATION: Synthetic

<400> SEQUENCE: 38
ggatttggca accttaacaa ggtggtgtt                                       29
```